United States Patent
Hietbrink et al.

(10) Patent No.: US 11,999,449 B2
(45) Date of Patent: Jun. 4, 2024

(54) ASSESSING AT LEAST ONE STRUCTURAL FEATURE OF AN ANTI-BIOFOULING ARRANGEMENT

(71) Applicant: KONINKLIJKE PHILIPS N.V., Eindhoven (NL)

(72) Inventors: Roelant Boudewijn Hietbrink, Utrecht (NL); Eduard Matheus Johannes Niessen, Ittervoort (NL); Antonius Adranus Petrus Schudelaro, Tilburg (NL); Rudy Roth, Helmond (NL)

(73) Assignee: Koninklijke Philips N.V., Eindhoven (NL)

( * ) Notice: Subject to any disclaimer, the term of this patent is extended or adjusted under 35 U.S.C. 154(b) by 396 days.

(21) Appl. No.: 17/601,092

(22) PCT Filed: Mar. 31, 2020

(86) PCT No.: PCT/EP2020/059145
§ 371 (c)(1),
(2) Date: Oct. 4, 2021

(87) PCT Pub. No.: WO2020/201293
PCT Pub. Date: Oct. 8, 2020

(65) Prior Publication Data
US 2022/0177086 A1 Jun. 9, 2022

(30) Foreign Application Priority Data
Apr. 2, 2019 (EP) .................................. 19166787.2

(51) Int. Cl.
*B63B 59/04* (2006.01)
*A61L 2/10* (2006.01)
(Continued)

(52) U.S. Cl.
CPC ................ *B63B 59/04* (2013.01); *A61L 2/10* (2013.01); *B08B 17/02* (2013.01); *B63B 79/10* (2020.01);
(Continued)

(58) Field of Classification Search
CPC . B63B 59/04; B63B 79/10; A61L 2/10; A61L 2202/11; A61L 2202/14;
(Continued)

(56) References Cited

U.S. PATENT DOCUMENTS

2017/0197693 A1 7/2017 Hietbrink et al.
2017/0262555 A1 9/2017 Omura
(Continued)

FOREIGN PATENT DOCUMENTS

EP 3406269 A1 11/2018
KR 20170030884 A 9/2015
(Continued)

OTHER PUBLICATIONS

International Search Report and Written Opinion From PCT/EP2020/059145 dated Oct. 8, 2020.

*Primary Examiner* — Anthony D Wiest

(57) ABSTRACT

In an anti-biofouling context, an anti-biofouling system (20) is provided, which is configured to emit anti-biofouling light in an activated state thereof and to be applied to an object (10). Further, the anti-biofouling system (20) comprises a sensor system (30) that is configured to obtain measurement data relating to at least one structural feature of an anti-biofouling arrangement (1) including both the anti-biofouling system (20) and the object (10) in an actual case of the anti-biofouling system (20) being in place on the object (10). By having the sensor system (30) as mentioned in the anti-biofouling system (20), it is achieved that one or more structural aspects of the anti-biofouling arrangement (1) may
(Continued)

be checked/monitored without a need for providing separate means for fulfilling such functionality.

13 Claims, 1 Drawing Sheet

(51) Int. Cl.
| | | |
|---|---|---|
| *B08B 17/02* | (2006.01) | |
| *B63B 79/10* | (2020.01) | |
| *G01B 11/00* | (2006.01) | |
| *G01L 1/22* | (2006.01) | |
| *G01N 29/04* | (2006.01) | |
| *G01N 33/2045* | (2019.01) | |
| *G01N 33/207* | (2019.01) | |

(52) U.S. Cl.
CPC ............ *G01B 11/002* (2013.01); *G01L 1/22* (2013.01); *G01N 29/04* (2013.01); *G01N 33/2045* (2019.01); *G01N 33/207* (2019.01); *A61L 2202/11* (2013.01); *A61L 2202/14* (2013.01); *G01N 2291/0234* (2013.01); *G01N 2291/0289* (2013.01); *G01N 2291/2675* (2013.01)

(58) Field of Classification Search
CPC ..... B08B 17/02; B08B 7/0057; G01B 11/002; G01B 7/16; G01L 1/22; G01N 29/04; G01N 33/2045; G01N 33/207; G01N 2291/0234; G01N 2291/0289; G01N 2291/2675

See application file for complete search history.

(56) References Cited

U.S. PATENT DOCUMENTS

| | | |
|---|---|---|
| 2018/0304321 A1 | 10/2018 | Visser et al. |
| 2020/0298292 A1 | 9/2020 | Paulussen |
| 2022/0177086 A1 | 6/2022 | Hietbrink |

FOREIGN PATENT DOCUMENTS

| | | |
|---|---|---|
| KR | 20160069368 A1 | 6/2016 |
| WO | 2003059732 A1 | 7/2003 |
| WO | 2010134022 A1 | 11/2010 |
| WO | 2014188347 A1 | 11/2014 |
| WO | 2017167629 A1 | 10/2017 |
| WO | 2017214688 A1 | 12/2017 |
| WO | 20180096214 A1 | 5/2018 |

ASSESSING AT LEAST ONE STRUCTURAL FEATURE OF AN ANTI-BIOFOULING ARRANGEMENT

CROSS REFERENCE TO RELATED APPLICATIONS

This application is a U.S. national phase application of International Application No. PCT/EP2020/059145 filed on Mar. 31, 2020, which claims the benefit of EP Application Serial No. 19166787.2 filed on Apr. 2, 2019 and are incorporated herein by reference.

FIELD OF THE INVENTION

In the first place, the invention relates to an anti-biofouling system configured to emit anti-biofouling light in an activated state thereof and to be applied to an object.

In the second place, the invention relates to an anti-biofouling arrangement including an object and an anti-biofouling system applied to the object, the anti-biofouling system being configured to emit anti-biofouling light in an activated state thereof.

In the third place, the invention relates to a method of applying an anti-biofouling system to an object in an anti-biofouling arrangement as mentioned.

In the fourth place, the invention relates to a method of obtaining information relevant to assessing at least one structural feature of an anti-biofouling arrangement as mentioned.

In the fifth place, the invention relates to a computer program product comprising code to cause a processor, when the code is executed on the processor, to execute the method as mentioned.

In the sixth place, the invention relates to a method of obtaining information relevant to designing a structure of an anti-biofouling arrangement as mentioned.

BACKGROUND OF THE INVENTION

Various structures which are temporarily or permanently exposed to an aqueous environment are prone to biofouling. For instance, in a marine environment (including both seawater and freshwater), ships, oil rigs, pipelines, support structures for sea-based wind turbines, structures for harvesting tidal/wave energy, etc. are subject to organisms growing on them, especially in areas which are temporarily or permanently exposed to water. As a result, the drag of ships increases, the moving of parts may be hampered, and filters may become clogged. In respect of the influence of biofouling on the drag of ships, it is noted that it may even be so that biofouling involves an increase of up to 40% in fuel consumption.

In general, biofouling is the accumulation of microorganisms, plants, algae, small animals and the like on surfaces. According to some estimates, over 1,800 species comprising over 4,000 organisms are responsible for biofouling. Hence, biofouling is caused by a wide variety of organisms, and involves much more than an attachment of barnacles and seaweeds to surfaces. Biofouling is divided into micro fouling that includes biofilm formation and bacterial adhesion, and macro fouling that includes the attachment of larger organisms. Due to the distinct chemistry and biology that determine what prevents them from settling, organisms are also classified as being hard or soft. Hard fouling organisms include calcareous organisms such as barnacles, encrusting bryozoans, mollusks, polychaetes and other tube worms, and zebra mussels. Soft fouling organisms include non-calcareous organisms such as seaweed, hydroids, algae and biofilm "slime". Together, these organisms form a fouling community.

As mentioned in the foregoing, biofouling creates substantial problems. Various solutions have been developed to address these problems. For instance, robots exist which are designed to scrape biofouling from the hulls of vessels. WO 2014/188347 A1 discloses another solution, namely a solution that involves applying an anti-biofouling layer to a surface that would otherwise be prone to biofouling, wherein the anti-biofouling layer is arranged for emitting ultraviolet light away from said surface. In this way, the risk of organisms growing on said surface (i.e. now the surface from which the ultraviolet light emanates) is reduced. Alternatively, a surface that is subject to biofouling may be irradiated with ultraviolet light, wherein it is to be noted that the solution according to WO 2014/188347 A1 is normally preferred for surfaces in water of low transparency to the ultraviolet light. In general, ultraviolet light of type C, i.e. UV-C light, is known for being effective when it comes to anti-biofouling so that good results may be achieved.

WO 2017/167629 discloses an anti-biofouling system in which an optical sensor is provided to monitor the degree of biofouling. The amount of UV radiation can then be controlled in dependence on the degree of biofouling, thereby to save energy during use of the system.

SUMMARY OF THE INVENTION

The Invention is Defined by the Claims.

According to the invention, an anti-biofouling system is provided, the anti-biofouling system being configured to emit anti-biofouling light in an activated state thereof and to be applied to an object, and the anti-biofouling system comprising a sensor system configured to obtain measurement data relating to at least one structural construction feature of an anti-biofouling arrangement including both the anti-biofouling system and the object in an actual case of the anti-biofouling system being in place on the object.

The invention involves an insight that it is possible to attribute an additional functionality to an anti-biofouling system for use with an object, particularly a functionality of obtaining measurement data relating to at least one structural feature of an anti-biofouling arrangement including both the anti-biofouling system and the object. In this way, it is achieved that it becomes even more interesting to use an anti-biofouling system with an object, as a way of assessing/monitoring at least one structural feature of the object is enabled without a need for separate means. Also, when the invention is applied, it is achieved that at least one structural feature of the anti-biofouling system and/or at least one structural feature of an actual combination of the anti-biofouling system and an object may be assessed/monitored if so desired. The invention does not involve all too complex measures and may be put to practice by adapting the design of a conventional anti-biofouling system so as to include one or more sensors configured to perform measurements on a structural level and any further components as may be necessary for power supply, data transfer etc.

In the context of the invention, the term "at least one structural feature of an anti-biofouling arrangement" is to be understood as referring to at least one feature that is directly related to at least one concrete aspect of the construction of the anti-biofouling arrangement. Hence, the term covers aspects of the construction of the anti-biofouling system as such, aspects of the construction of the object as such, and aspects of the construction of the combination of the anti-biofouling system and the object such as aspects relating to a coupling between at least one unit of the anti-biofouling system and the object. It follows from the foregoing that the term "at least one structural feature of an anti-biofouling arrangement" at least covers aspects both relating to the construction of the anti-biofouling arrangement and being of a mechanical nature.

The construction of the anti-biofouling arrangement as such relates to physical and mechanical characteristics of the anti-biofouling arrangement, including initially before application to the object. The construction of the object as such relates to physical and mechanical characteristics of the object including initially before the anti-biofouling arrangement is applied to the object, and before biofouling. The construction of the combination of the anti-biofouling system and the object relates to the interface between the anti-biofouling system and the object, including the interface characteristics initially before before exposure to biofouling. In use, this interface is not intended to be exposed to biofouling because the object surface is covered by the anti-biofouling arrangement. The structural construction feature is thus a mechanical characteristic which is initially established as part of the construction of the anti-biofouling arrangement, or of the object, or of the combination of the object and the anti-biofouling arrangement. In each case, such structural construction feature is initially established prior to exposure to the biofouling and hence prior to biofouling treatment. The evolution of the structural construction feature may then be monitored, for example to detect structural damage or decay.

The invention is not restricted to any particular timing of the process of obtaining measurement data relating to at least one structural feature of the anti-biofouling arrangement. The process may be a continuous, ongoing process, or may be a discontinuous process in which measurements are performed at regular or irregular intervals, in an automated manner or on demand.

The invention is suitable to be applied in various fields including the field of marine structures. Examples of objects with which the anti-biofouling system according to the invention may be used include ships and other vessels, marine stations, sea-based oil or gas installations, buoyancy devices, support structures for wind turbines at sea, structures for harvesting wave/tidal energy, sea chests, underwater tools, etc. In general, it is noted that the invention is not only suitable to be applied in a context of objects for use in seawater, but may involve advantages in respect of any object for use in any type of water that is known to contain biofouling organisms.

As implied in the foregoing, the at least one structural feature of the anti-biofouling arrangement in relation to which measurement data may be obtained by means of the sensor system may be at least one structural feature of the object. For example, the sensor system may be configured to inspect the condition of an exterior surface of the object so as to detect any damage to the exterior surface and/or may be configured to look further down into the object, such as for the purpose of assessing the mechanical integrity of a part of the object and/or may be configured to check whether or not a protruding component of the object is present, and if the component is found to be present, indeed, to check whether or not any possible coupling between the component and the remainder of the object is intact. Numerous other feasible functionalities of the sensor system are available and covered by the invention as well.

It may be practical for the sensor system to comprise at least one strain gauge configured to assess mechanical deformation of the object and/or at least one structural unit of the anti-biofouling system, and/or at least one ultrasound sensor configured to assess mechanical integrity of at least one area of the object, for example. In respect of the possible use of a strain gauge as mentioned, it is noted that when it is desired to obtain information about mechanical deformation of an object, this may be done in a direct manner by performing strain measurements directly on the object and/or in an indirect manner by performing strain measurements in an anti-biofouling system applied to the object. An ultrasound sensor as mentioned may be used for assessing the condition of welding seams on a metal cover or the like of an object, for example.

In general, the sensor system may comprise any suitable type(s) of sensor for checking the object for at least one structural feature, and more in general, the sensor system may comprise any suitable type(s) of sensor for checking the object and/or (at least one structural unit of) the anti-biofouling system, and/or a structural interaction between the object and the anti-biofouling system for at least one structural feature. In this respect, it is noted that in addition to or as an alternative to the option of the at least one structural feature of the anti-biofouling arrangement in relation to which measurement data may be obtained by means of the sensor system being at least one structural feature of the object, the invention covers at least one of the options of the at least one structural feature as mentioned being at least one structural feature of the anti-biofouling system and the at least one structural feature as mentioned being at least one structural feature of the anti-biofouling arrangement at an interface of the object and the anti-biofouling system.

When the at least one structural feature is to be checked at an interface of the object and the anti-biofouling system, it may be practical for the sensor system to comprise at least one UV sensor configured to assess adherence and/or positioning of at least one structural unit of the anti-biofouling system with respect to the object. This is based on the insight that if, for instance, a structural unit of the anti-biofouling system begins to become detached from the object, this may cause a detectable change in the reflection of ultraviolet light at the interface of the object and the structural unit.

The sensor system may further be configured to obtain measurement data relating to a degree of biofouling of at least an area of the anti-biofouling arrangement. For example, a UV sensor that is used to assess adherence and/or positioning of at least one structural unit of the anti-biofouling system with respect to the object, as described in the foregoing, may have an additional function in performing biofouling inspections. It may be very advantageous to have a minimum of components in an anti-biofouling arrangement. Nevertheless, the invention also covers options according to which at least one sensor is dedicated to performing a check of at least one structural feature in an anti-biofouling arrangement and at least one other sensor is dedicated to performing a check of a biofouling extent on one or more areas in the arrangement.

It may be practical for the anti-biofouling system according to the invention to comprise at least two discrete structural units. An example of a case in which the option of having a number of structural units may be advantageous is a case in which the object has a surface of large dimensions and the anti-biofouling system is to be applied to that surface. The structural units as mentioned may for instance be substantially size-limited in two orthogonal directions perpendicular to a thickness direction of the anti-biofouling system, i.e. in two directions along the surface, in which case the structural units may be referred to as anti-biofouling tiles, or substantially size-limited in only one direction perpendicular to the thickness direction of the anti-biofouling system, in which case the structural units may be referred to as anti-biofouling strips. The anti-biofouling tiles and strips and mentioned may be so thin that they may have a foil-like appearance.

The optional structural units of the anti-biofouling system may be of any suitable design. For example, at least one structural unit may include a slab of material that is transparent to anti-biofouling light. The slab of material may have a function in transporting/guiding light shining from one or more light sources in an activated state, and may comprise a light-outcoupling surface having any suitable surface structure. In such a case, the one or more light sources may be associated with the slab of material in any suitable way. For example, it may be practical for the one or more light sources to be embedded in the slab of material. This is one way of realizing an embodiment of the anti-biofouling system according to the invention according to which the system is configured to emit the anti-biofouling light away from the object in the anti-biofouling arrangement.

The anti-biofouling light may be ultraviolet light, particularly ultraviolet light of the UV-C type, which does not imply that other types of anti-biofouling light are not covered by the invention as well. The anti-biofouling system may comprise one or more light sources of any suitable type. For example, the anti-biofouling system may comprise a layer of material that can be activated to emit light. On the other hand, it is possible for the anti-biofouling system to comprise a number of discrete light emitters such as LEDs.

In conformity with the foregoing, it is noted that the invention also relates to an anti-biofouling arrangement including an object and an anti-biofouling system applied to the object, the anti-biofouling system being configured to emit anti-biofouling light in an activated state thereof, and the anti-biofouling system comprising a sensor system configured to obtain measurement data relating to at least one structural feature of the anti-biofouling arrangement. Particulars of the anti-biofouling system addressed in the foregoing are equally applicable in the context of the anti-biofouling arrangement. The object may be of any shape and size, and may comprise any type of material. For example, the object may include an electrically conductive surface to which at least one structural unit of the anti-biofouling system is applied, in which case the object may have a function in transport of electric power that can be used for operating the anti-biofouling system, wherein the anti-biofouling system may be equipped with a coil system or any other system that is configured to enable the anti-biofouling system to be supplied with electric power. One practical example of the object is a vessel, in which case at least one structural unit of the anti-biofouling system may be applied to the vessel at the position of at least an area of the vessel's hull.

In a practical embodiment of the anti-biofouling arrangement according to the invention, the arrangement is equipped with a processor that is configured to receive and process measurement data from the sensor system of the anti-biofouling system and to provide output representative of the at least one structural feature of the anti-biofouling arrangement to which the measurement data relate. The output may be interpreted in an automated manner and/or by one or more persons, such as to determine whether any action of some kind needs to be taken and/or to gain knowledge about design aspects of a structure of an anti-biofouling arrangement that may be used to improve future embodiments of such an arrangement.

In another aspect, the invention relates to a method of applying an anti-biofouling system to an object in an anti-biofouling arrangement as mentioned, wherein at least one structural unit of the anti-biofouling system is positioned and fixed with respect to the object.

Further, the invention relates to a method of obtaining information relevant to assessing at least one structural feature of an anti-biofouling arrangement as mentioned, comprising the following steps: receiving and processing measurement data obtained from the sensor system of the anti-biofouling system, and providing output representative of the at least one structural feature of the anti-biofouling arrangement to which the measurement data relate. A computer program product comprising code to cause a processor, when the code is executed on the processor, to execute this information obtaining method is also covered by the invention.

Still further, the invention relates to a method of obtaining information relevant to designing a structure of an anti-biofouling arrangement as mentioned, comprising the following steps: obtaining output representative of at least one structural feature of at least two different actual anti-biofouling arrangements by performing the above-mentioned information obtaining method in respect of the at least two different actual anti-biofouling arrangements, processing the output representative of the at least one structural feature of the at least two different actual anti-biofouling arrangements, and providing output representative of a trend of the at least one structural feature of the at least two different actual anti-biofouling arrangements. Such a method may be applied as part of a process aimed at determining how a practical design of an anti-biofouling arrangement, i.e. a practical design of an object and/or an anti-biofouling system and/or an interface/coupling between an object and an anti-biofouling system, may be improved, at least as far as the structural aspects thereof are concerned.

In the context of the invention, a data-gathering system may be used for collecting/storing measurement data relating to at least one structural feature of an anti-biofouling arrangement obtained by means of the sensor system of an anti-biofouling system that is part of the anti-biofouling arrangement and/or information based on such data.

The above-described and other aspects of the invention will be apparent from and elucidated with reference to the following detailed description of a basic embodiment of an anti-biofouling arrangement including an object and an anti-biofouling system that is applied to the object and that is configured to emit anti-biofouling light in an activated state thereof.

BRIEF DESCRIPTION OF THE DRAWINGS

The invention will now be explained in greater detail with reference to the figures, in which equal or similar parts are indicated by the same reference signs, and in which.

Figure 1:
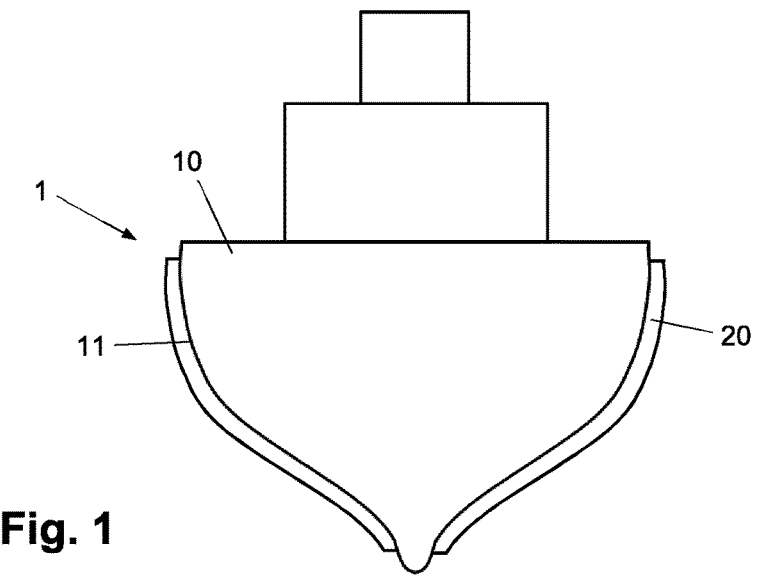
FIG. 1 diagrammatically shows a sectional view of a ship and an anti-biofouling system arranged on the ship's hull, and FIG. 2 diagrammatically shows a portion of the ship's hull and the anti-biofouling system in enlarged view.

For the sake of illustration, the anti-biofouling system is depicted in an exaggeratedly thick fashion in the figures.

DETAILED DESCRIPTION OF THE EMBODIMENTS

With reference to the figures, it is noted that a feasible embodiment of an anti-biofouling arrangement 1 according to the invention comprises a ship 10 and an anti-biofouling system 20 arranged on the ship's hull 11. At the position of the hull 11, the ship 10 is to be subjected to an anti-biofouling action, in order to avoid formation of biofouling deposits on the hull 11 and to thereby avoid an increase of drag of the ship 10. In particular, the anti-biofouling arrangement 1 is designed to have an anti-biofouling action on the ship 10 on the basis of light radiation, continuously or from time to time, wherein it is to be noted that in order to achieve good anti-fouling effects, the light may be ultraviolet light, especially UV-C light.

As mentioned, the anti-biofouling system 20 is arranged on the hull 11. The anti-biofouling system 20 may be a type of system that is suitable to be used for realizing anti-biofouling effects on an object by emitting anti-biofouling light in a direction away from the object, as known from WO 2014/188347 A1, for example. Such a system may include a number of light sources 21 configured to generate anti-biofouling light. A practical example of such light sources 21 is UV-C LEDs.

Figure 2:
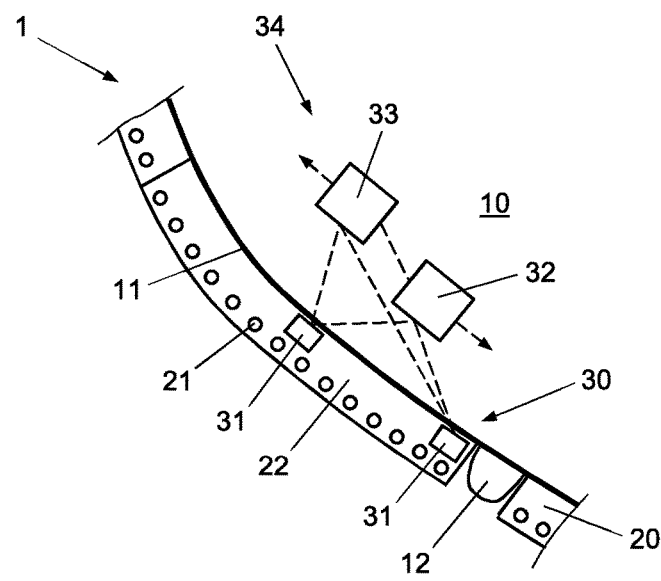

The anti-biofouling system 20 may comprise material that is transparent to the anti-biofouling light, that may have a structural function in embedding the light sources 21, for example, or supporting the light sources 21 in another way, and that may be arranged so as to cover areas of the hull 11. The transparent material may be provided in various slabs, in which case the anti-biofouling system 20 may be realized as a collection of structural units 22 such as tiles or strips, for example, as illustrated in FIG. 2, wherein the thickness of the slabs of the transparent material may be so small, even in the millimeter range, that the slabs can normally be referred to as pieces of foil. During operation of the light sources 21, the transparent material may have a function in transporting the generated anti-biofouling light along the hull 11 and ensuring that the anti-biofouling light is more or less evenly spread across the hull 11, i.e. may serve as a light guide, wherein the anti-biofouling light is outcoupled from the light guide at various positions, in a direction away from the ship 10. A phenomenon like total internal reflection may contribute to the transportation of the light through the transparent material. A practical example of the transparent material is a silicone material.

In general, a surface subject to biofouling is not necessarily planar/flat, but may instead be curved in one or more directions and include one or more convexly curved areas and/or concavely curved areas. A ship's hull 11 is an example of a curved surface. Further, protrusions may be arranged on the surface, which protrusions may or may not be part of the anti-biofouling system 20. Examples of protrusions in the context of a ship 10 include a fin (not shown) on the ship's hull 11, a welding seam 12 on the ship's hull 11, as illustrated in FIG. 2, and a protrusion (not shown) arranged to protect the anti-biofouling system 20 against impacts of external objects such as tree trunks floating in water.

According to a notable aspect of the invention, the anti-biofouling system 20 comprises a sensor system 30 configured to obtain measurement data relating to at least one structural feature of the anti-biofouling arrangement 1. In case the anti-biofouling system 20 comprises a plurality of structural units 22, it may be so that each of those units 22 is provided with one or more sensors 31 and associated means such as means for powering the sensors 31. However, this is not necessary, and it may also be so that the sensor system 30 is manifested in only one or a limited number of structural units 22. In any case, it may be so that the one or more sensors 31 and/or one or more other components of the sensor system 30 are integrated in (a structural unit 22 of) the anti-biofouling system 20. For example, assuming that the anti-biofouling system 20 comprises slabs of transparent material, the sensor(s) 31 and/or the other component(s) may be embedded in one or more of those slabs. The sensor system 30 of the anti-biofouling system 20 may comprise just one type of sensor or at least two different types of sensor, depending on the number and kind of structural features of the anti-biofouling arrangement 1 that should be assessed.

Power supply as necessary for actually realizing the sensing functionality of the anti-biofouling system 20 may be realized in any suitable way, and the same is applicable in respect of the light-emitting functionality of the anti-biofouling system 20. As indicated in FIG. 2, the anti-biofouling arrangement 1 may further comprise a processor 32 for receiving and processing measurement data from the sensor system 30 and for providing output representative of the at least one structural feature of the anti-biofouling arrangement 1 to which the measurement data relate. Further, a data-gathering system 33 may be provided for receiving and storing the measurement data and/or output from the processor 32. Various data transfer possibilities are indicated in FIG. 2 by means of dashed lines and arrows. The processor 32 and the data-gathering system 33 are part of a data analysis system 34 that may optionally include further components.

The invention offers a wide variety of possibilities when it comes to using the sensor system 30 for the purpose of obtaining measurement data relating to at least one structural feature of the anti-biofouling arrangement 1. A number of practical examples is listed below.

In the first place, the sensor system 30 may be configured to obtain measurement data relating to at least one structural feature of the ship 10. It may be desirable to have information about the way in which the ship 10 deforms under certain circumstances and/or information about whether or not metal fatigue occurs in one or more areas and/or information about whether or not hair cracks are present in one or more areas and/or information about the condition of welding seams 12 on the hull 11, etc.

In the second place, the sensor system 30 may be configured to obtain measurement data relating to at least one structural feature of the anti-biofouling system 20. It may be desirable to have information about whether or not a structural unit 22 is deformed and/or damaged, for example. In such a case, the anti-biofouling system 20 may be denoted as being a system having a self-diagnosing functionality when it comes to assessing the condition of the system at a structural level.

In the third place, the sensor system 30 may be configured to obtain measurement data relating to at least one structural feature of the anti-biofouling arrangement 1 at an interface of the ship 10 and the anti-biofouling system 20. It may be desirable to have information about whether or not the anti-biofouling system 20 is still in a correct position with respect to the ship's hull 11 and attached properly to the ship's hull 11, for example.

The sensor system 30 may comprise one or more suitable types of sensor, and may include as many sensors 31 as necessary for realizing one or more functionalities as envisaged. The sensors 31 may be configured to perform a sensing action in a certain direction, in a limited number of directions, or a range of directions, on an area of any possible size, a limited number of areas, or a range of areas. By means of the sensor system 30, it is possible to perform a continuous monitoring process and/or single checks, on a regular or irregular basis, in an automated fashion or on demand, of one or more vital structural features of an anti-biofouling arrangement 1. It may be beneficial for the anti-biofouling system 20 to have a function in checking if biofouling deposits are present in one or more areas of the anti-biofouling arrangement 1, such as on an exterior surface of the anti-biofouling system 20, and if this is found to be the case, indeed, in determining a quantitative factor of the biofouling. To that end, the anti-biofouling system 20 may be equipped with another sensor system (not shown), or one or more sensors 31 which are included in the sensor system 30 that is configured to obtain measurement data relating to at least one structural feature of the anti-biofouling arrangement 1 may have a dual functionality, i.e. may be suitable to be used for both obtaining measurement data relating to at least one structural feature of the anti-biofouling arrangement 1 and obtaining biofouling measurement data. In this respect, it is noted that a UV sensor is an example of a sensor that may have a dual functionality as mentioned, as such a sensor is suitable to be applied for checking adherence of a structural unit 22 of the anti-biofouling system 20 to the ship's hull 11 at one side of the structural unit 22 and for checking biofouling of the structural unit 22 at the opposite side of the structural unit 22.

In the framework of the invention, the measurement data which are obtained when the sensor system 30 is operated may be used further in any suitable way, wherein it may be practical to process the measurement data, which does not alter the fact that direct interpretation of the measurement data may be possible as well in particular cases. Not only may the measurement data be used for determining an actual status or predicting a future status of one or more structural aspects of an anti-biofouling arrangement 1, also the measurement data may be used in processes aimed at discovering trends related to various structural measures so that possibilities of improving structural aspects of the anti-biofouling arrangement 1 on a design level may be created.

It will be clear to a person skilled in the art that the scope of the invention is not limited to the examples discussed in the foregoing, but that several amendments and modifications thereof are possible without deviating from the scope of the invention as defined in the attached claims. It is intended that the invention be construed as including all such amendments and modifications insofar they come within the scope of the claims or the equivalents thereof. While the invention has been illustrated and described in detail in the figures and the description, such illustration and description are to be considered illustrative or exemplary only, and not restrictive. The invention is not limited to the disclosed embodiments. The drawings are schematic, wherein details which are not required for understanding the invention may have been omitted, and not necessarily to scale.

Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. Any reference signs in the claims should not be construed as limiting the scope of the invention.

Elements and aspects discussed for or in relation with a particular embodiment may be suitably combined with elements and aspects of other embodiments, unless explicitly stated otherwise. Thus, the mere fact that certain measures are recited in mutually different dependent claims does not indicate that a combination of these measures cannot be used to advantage.

The term "comprise" as used in this text will be understood by a person skilled in the art as covering the term "consist of". Hence, the term "comprise" may in respect of an embodiment mean "consist of", but may in another embodiment mean "contain/include at least the defined species and optionally one or more other species".

Notable aspects of the invention can be summarized as follows. In an anti-biofouling context, an anti-biofouling system 20 is provided, which is configured to emit anti-biofouling light in an activated state thereof and to be applied to an object 10. Further, the anti-biofouling system 20 comprises a sensor system 30 that is configured to obtain measurement data relating to at least one structural feature of an anti-biofouling arrangement 1 including both the anti-biofouling system 20 and the object 10 in an actual case of the anti-biofouling system 20 being in place on the object 10. One of the benefits of having the sensor system 30 as mentioned in the anti-biofouling system 20 resides in the insight that the anti-biofouling system 20 is intended to be combined with the object 10 to an anti-biofouling arrangement 1 anyway and may therefore be used for the purpose of checking/monitoring one or more structural aspects of such anti-biofouling arrangement 1 without a need for separate means for fulfilling such functionality.

The invention claimed is:

1. Anti-biofouling arrangement including:
    an object; and
    an anti-biofouling system configured to emit anti-biofouling light in an activated state thereof, the anti-biofouling system being applied to the object and having a structural unit which is positioned and fixed with respect to the object,
    the anti-biofouling system comprising a sensor system,
    wherein the sensor system configured to obtain measurement data relating to a structural construction feature relating to the construction of the anti-biofouling arrangement.

2. The anti-biofouling arrangement according to claim 1, wherein the at least one structural construction feature is a structural feature of the object.

3. The anti-biofouling arrangement according to claim 1, wherein the at least one structural construction feature is a structural feature of the anti-biofouling system.

4. The anti-biofouling arrangement according to claim 1, wherein the sensor system comprises a strain gauge configured to assess mechanical deformation of the object and/or the structural unit, and/or an ultrasound sensor configured to assess mechanical integrity of an area of the object.

5. The anti-biofouling arrangement according to claim 1, wherein the structural construction feature is a structural feature at an interface of the object and the anti-biofouling system.

6. The biofouling arrangement according to claim 5, wherein the sensor system comprises at least one UV sensor configured to assess adherence and/or positioning of the structural unit with respect to the object.

7. The biofouling arrangement according to claim 1, wherein the sensor system is further configured to obtain measurement data relating to a degree of biofouling of an area of the anti-biofouling arrangement.

8. The anti-biofouling arrangement according to claim 1, configured to emit the anti-biofouling light away from the object in the anti-biofouling arrangement.

9. The anti-biofouling arrangement according to claim 1, wherein the object is a vessel, and wherein the structural unit is applied to an area of the vessel's hull.

10. The anti-biofouling arrangement according to claim 9, comprising a processor configured to receive and process measurement data from the sensor system of the anti-biofouling system and to provide output representative of the structural feature to which the measurement data relate.

11. Method of applying an anti-biofouling system to an object to obtain an anti-biofouling arrangement according to claim 1, comprising a step of positioning and fixing the structural unit to the object.

12. Method of obtaining information relevant to assessing the structural construction feature of an anti-biofouling arrangement according to claim 1, comprising the following steps:
   receiving and processing measurement data obtained from the sensor system, and
   providing output representative of the structural construction feature to which the measurement data relate.

13. Computer program product comprising code to cause a processor, when the code is executed on the processor, to execute the method according to claim 12.

* * * * *